Nov. 21, 1950 V. R. DE PETRIS Plant Pat. 988
CHRYSANTHEMUM PLANT
Filed May 11, 1949
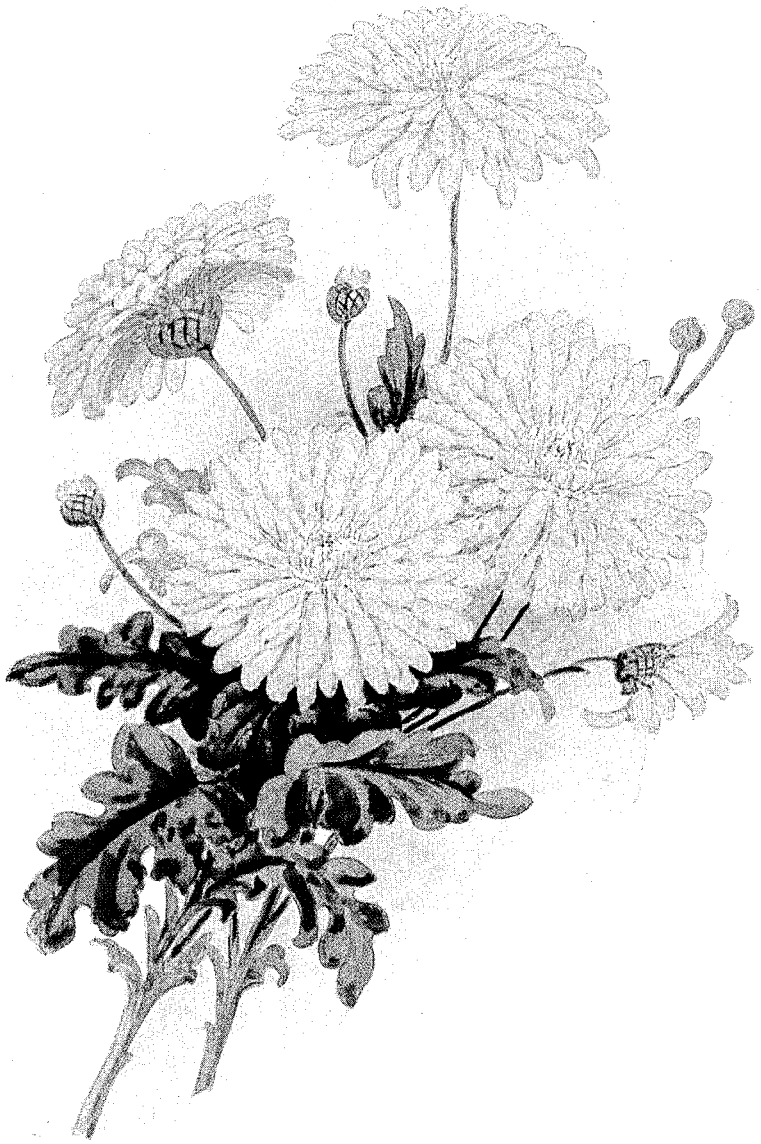
WITNESS
Addison E. Avery
INVENTOR
VINCENT R. DEPETRIS,
by Rummler Rummler & Snow,
ATTYS.

Patented Nov. 21, 1950

Plant Pat. 988

UNITED STATES PATENT OFFICE

988

CHRYSANTHEMUM PLANT

Vincent R. DePetris, Grosse Pointe Farms, Mich., assignor to DePetris, Inc., a corporation of Michigan Application May 11, 1949, Serial No. 92,625

1 Claim. (Cl. 47—60)

The present discovery relates to a new and distinct variety of chrysanthemum plant which was the result of a succession of definite breeding efforts carried on by me since 1922. This new variety has been reproduced by me at Grosse Pointe, Michigan, by cuttings and budding through several generations and its characteristics appear to be permanently fixed.

In obtaining the results, I crossed the variety "Verona" with the pollen of "Aviator," thus combining the desirable characteristics of two very hardy varieties, *C. nipponicum* and *C. articum*.

The primary object in carrying out this invention was to fix the peculiar warm and unusual color which is largely the distinguishing characteristic of the new variety.

Furthermore, the plant is a vigorous and hardy variety having distinct growth habits characterized by many upright long stems, and quite resistant to many diseases. Its flowers have a perfect double form and are of medium size carried on well-formed sprays with rigid petioles.

The accompanying illustration shows the blooms and foliage in their natural colors but in arbitrary arrangement as cut flowers.

The following is a detailed description of this new variety:

Classification: Chrysanthemum.

Botanic strain: *Artic nipponicum* hybrid.

Parentage: Seedling.

*Seed parent.*—Verona.

*Pollen parent.*—Aviator.

Plant:

*Form.*—Herbacious, sub-shrubby and erect branching.

*Height.*—32 to 36 inches.

*Growth.*—Vigorous, rugged and robust.

Stems: Length—30 to 36 inches. Sturdy and woody at base.

Foliage: Abundant in quantity.

*Color.*—New foliage—glossy green. Old foliage—very dark glossy green.

*Size of leaf.*—Medium.

*Texture.*—Leathery and smooth.

*Shape.*—Incised deeply.

Flower: Blooms profusely from end of September on.

*Size.*—About 3 inches across.

*Borne.*—In clusters of single blooms at the ends of long peduncles.

*Petalage.*—Double. Outer petals are broad and long overlaid with layers of shorter petals radiating from a central disk of genital organs and florets.

*Color.*—Raspberry-apricot shading to bronze. Anthers—Yellow.

*Texture.*—Leathery.

*Appearance.*—Velvety.

Not affected by wet or hot weather.

*Persistence (hang on and dry).*—Long lasting.

*Disease resistance.*—Very good.

*Lasting quality.*—On plant—excellent. As a cut flowers—excellent.

The color designations according to Maerz and Paul are:

Inner petals, Apricot, Plate 10–F–7.

Outer and predominating petals, Bronze Raspberry, Plate 3–H–10.

Reverse of petals, Bronze Tan, Plate 12–L–9.

Foliage, Dark Green, Plate 23–L–7.

This new variety is easily distinguished from other varieties by its distinct habit of growth, having many rigid upright stems averaging 36 inches in length which makes it ideal for cutting. The foliage is distinctly very dark green, glossy and leathery. The blooms are large and of a well-shaped double form carried on well formed sprays with rigid petioles. The color is most unusual and can best be described as a glowing raspberry-apricot. It has a long blooming period and the flowers are long lasting. It is a vigorously growing variety, quite resistant to many diseases. The distinctiveness of this variety is due to the inherited strains of *C. nipponicum* and *C. articum* combined with some of the hortorum varieties. Its flowers have a perfectly formed double petalage of medium size, but its novel color is its most outstanding characteristic.

Having thus disclosed the invention, I claim:

A new and distinct variety of chrysanthemum plant characterized as to novelty by the unusual and distinctive raspberry-apricot coloring of its blooms, its habit of growth, sturdy upright stems, and glossy dark green leaves, substantially as shown and described.

VINCENT R. DE PETRIS.

No references cited.